(12) United States Patent
Chen et al.

(10) Patent No.: US 10,651,507 B2
(45) Date of Patent: May 12, 2020

(54) MINIATURIZED ELECTRONICS PACKAGE WITH PATTERNED THIN FILM SOLID STATE BATTERY

(71) Applicant: INTERNATIONAL BUSINESS MACHINES CORPORATION, Armonk, NY (US)

(72) Inventors: Qianwen Chen, Yorktown Heights, NY (US); Bing Dang, Chappaqua, NY (US); John U. Knickerbocker, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 36 days.

(21) Appl. No.: 15/802,109

(22) Filed: Nov. 2, 2017

(65) Prior Publication Data

US 2018/0323473 A1    Nov. 8, 2018

Related U.S. Application Data

(63) Continuation of application No. 15/585,924, filed on May 3, 2017.

(51) Int. Cl.

| | | |
|---|---|---|
| *H01M 10/0585* | (2010.01) | |
| *H01M 10/0525* | (2010.01) | |
| *A61B 5/00* | (2006.01) | |
| *H01M 10/04* | (2006.01) | |
| *H01M 10/052* | (2010.01) | |

(52) U.S. Cl.
CPC ......... *H01M 10/0585* (2013.01); *A61B 5/681* (2013.01); *A61B 5/6861* (2013.01); *H01M 10/0436* (2013.01); *H01M 10/052* (2013.01); *A61B 2560/0214* (2013.01); *A61B 2562/125* (2013.01); *A61B 2562/166* (2013.01)

(58) Field of Classification Search
CPC ......... H01M 10/0585; H01M 10/0525; H01M 2220/30; A61B 5/681; A61B 5/6861; A61B 2562/166; A61B 2562/125; A61B 2560/0214
See application file for complete search history.

(56) References Cited

U.S. PATENT DOCUMENTS

| | | |
|---|---|---|
| 6,764,525 B1 | 7/2004 | Whitacre et al. |
| 6,866,901 B2 | 3/2005 | Burrows et al. |
| 7,045,246 B2 | 5/2006 | Simburger et al. |
| 9,325,007 B2 | 4/2016 | Kwak et al. |
| 9,472,789 B2 | 10/2016 | Andry et al. |
| 2003/0064292 A1 | 4/2003 | Neudecker et al. |
| 2004/0258984 A1 | 12/2004 | Ariel et al. |
| 2005/0079418 A1 | 4/2005 | Kelley et al. |
| 2011/0294015 A1 | 12/2011 | Pirk et al. |
| 2015/0287672 A1* | 10/2015 | Yazdani ............... H01L 21/486 257/414 |
| 2015/0287960 A1 | 10/2015 | Andry et al. |
| 2016/0190564 A1* | 6/2016 | Samarao ............... H01M 4/134 429/320 |
| 2017/0069883 A1* | 3/2017 | Jarry ................... H01M 2/0207 |
| 2017/0324068 A1* | 11/2017 | Andry ................. H01M 2/0207 |

OTHER PUBLICATIONS

G.J.Dolan et al., "Offset Masks for Lift-Off Photoprocessing," Applied Physics Letters, vol. 31, No. 5. Sep. 1, 1977. pp. 337-339.
List of IBM Patents or Patent Applications Treated as Related dated Nov. 2, 2017, 2 pages.

* cited by examiner

*Primary Examiner* — Muhammad S Siddiquee
(74) *Attorney, Agent, or Firm* — Tutunjian & Bitetto, P.C.; Vazken Alexanian

(57) ABSTRACT

A method for integrating a thin film microbattery with electronic circuitry includes forming a release layer over a handler, forming a thin film microbattery over the release layer of the handler, removing the thin film microbattery from the handler, depositing the thin film microbattery on an interposer, forming electronic circuitry on the interposer, and sealing the thin film microbattery and the electronic circuitry to create individual microbattery modules.

6 Claims, 9 Drawing Sheets

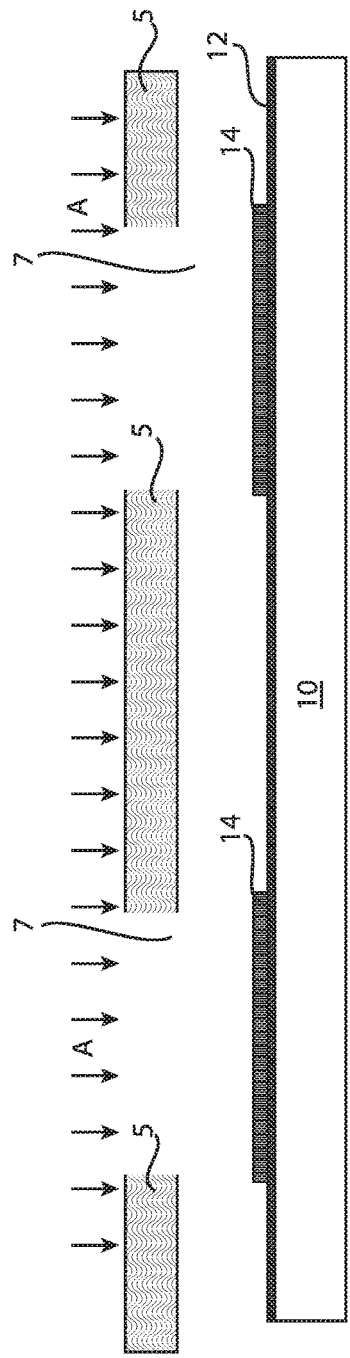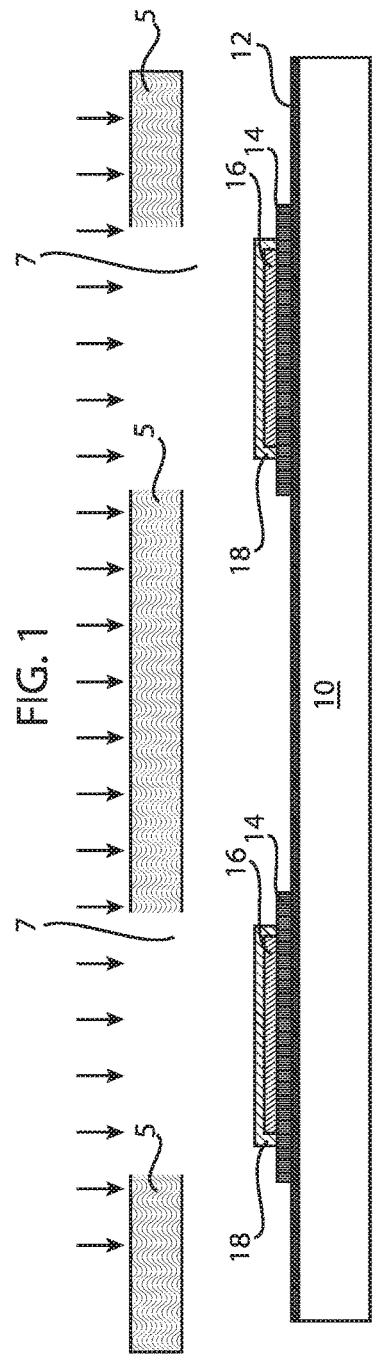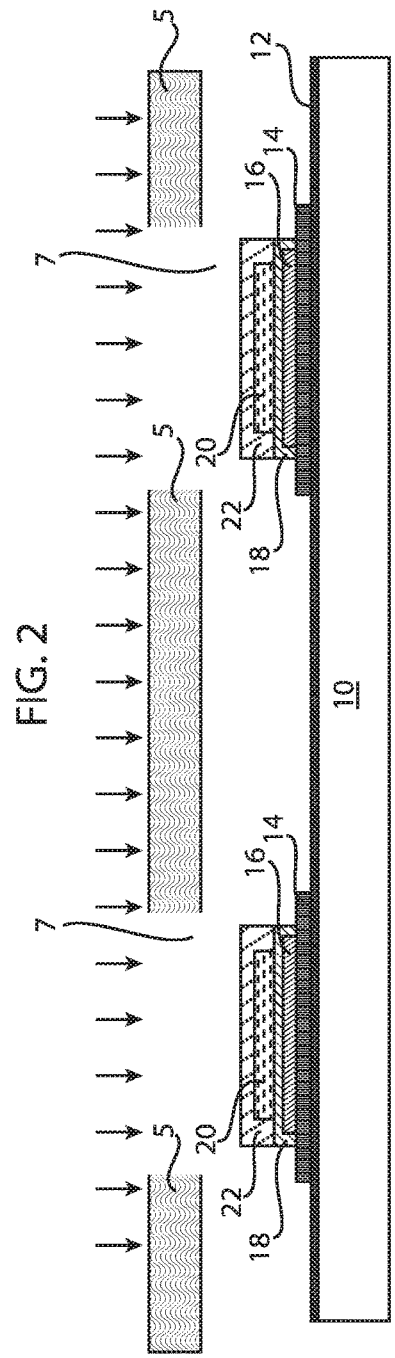

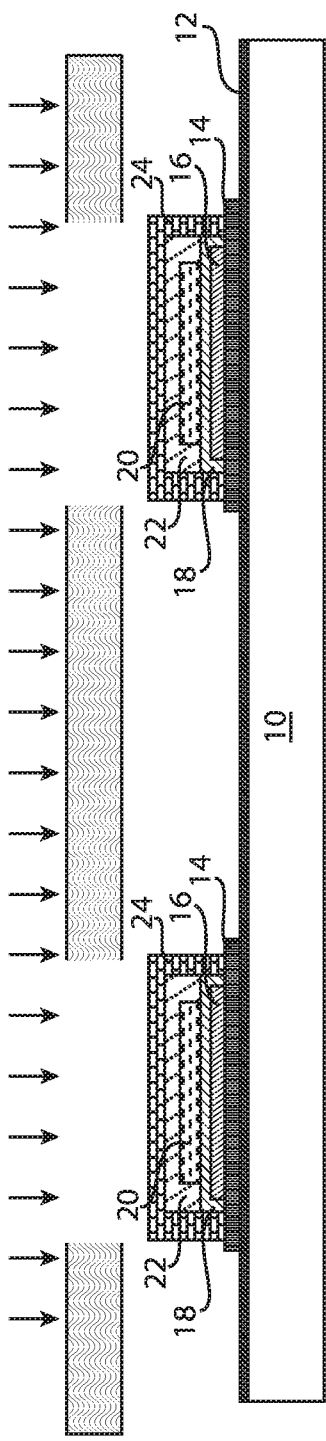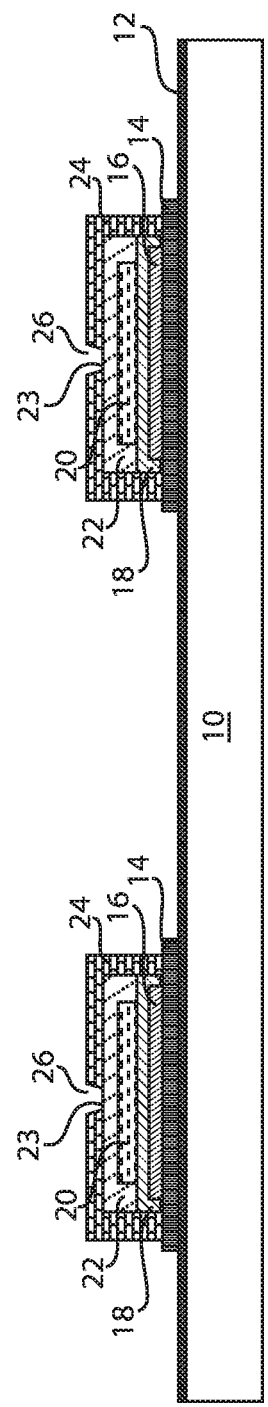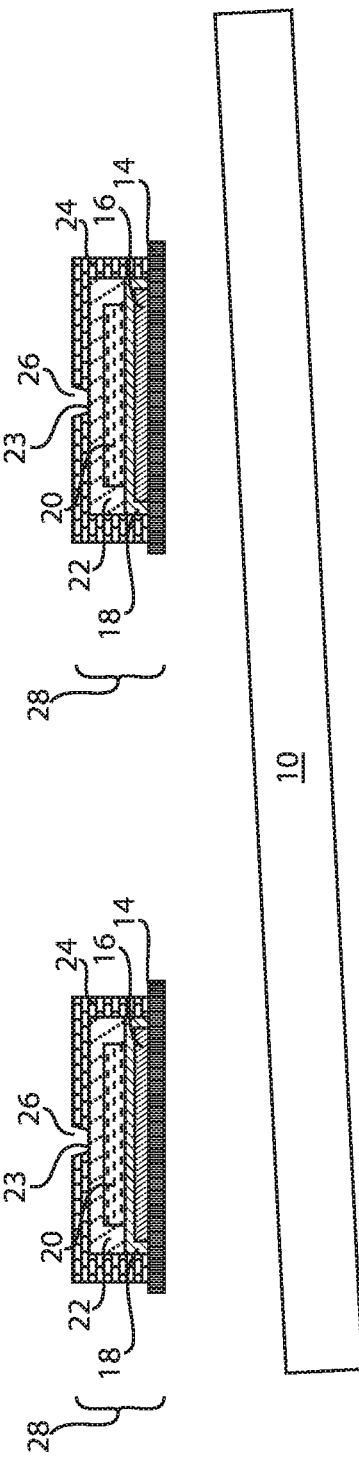

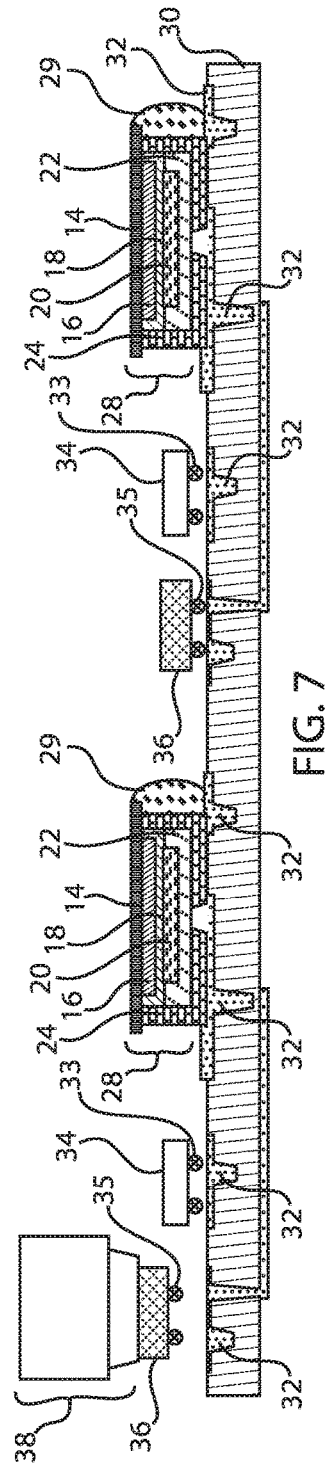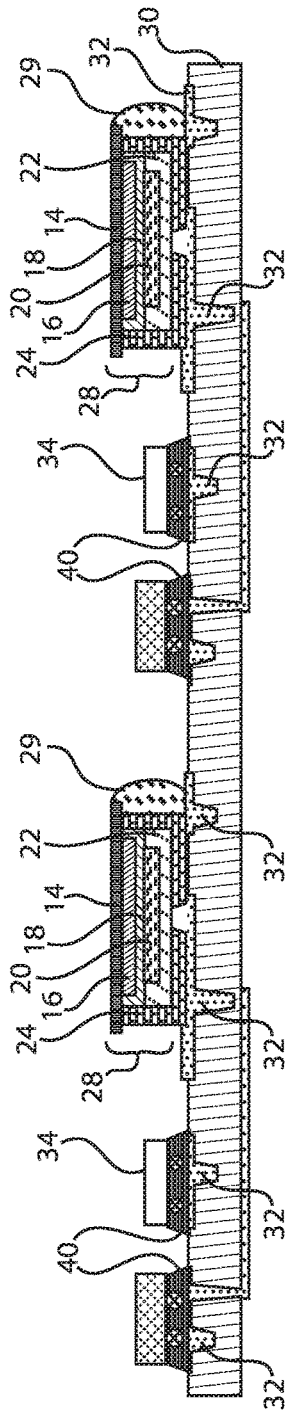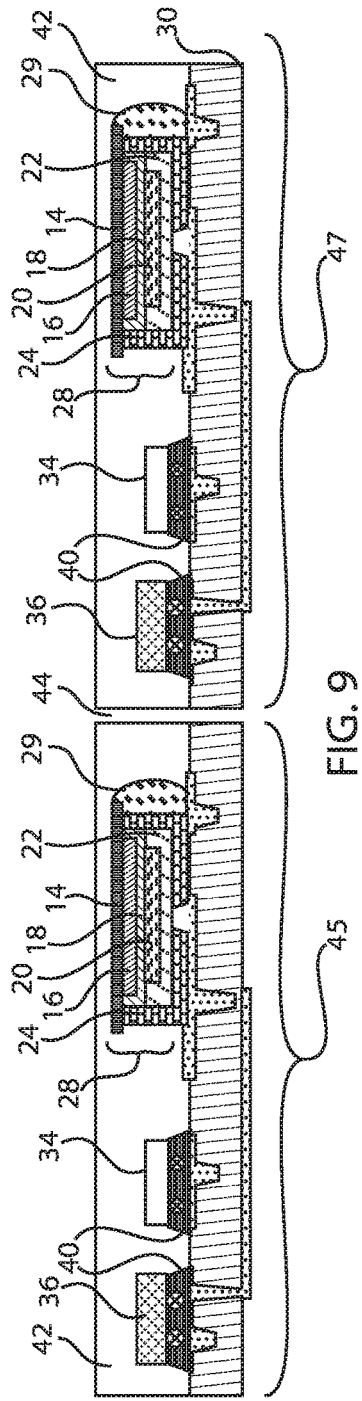
FIG. 7
FIG. 8
FIG. 9

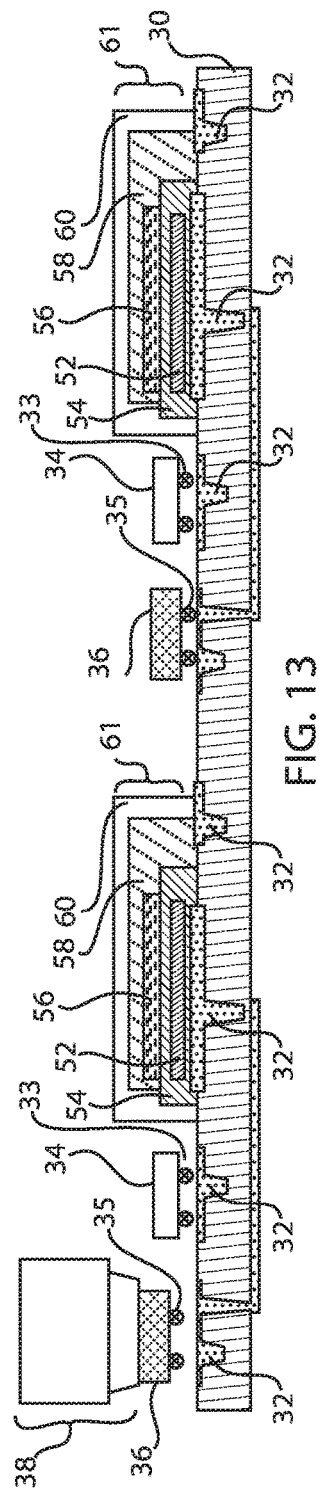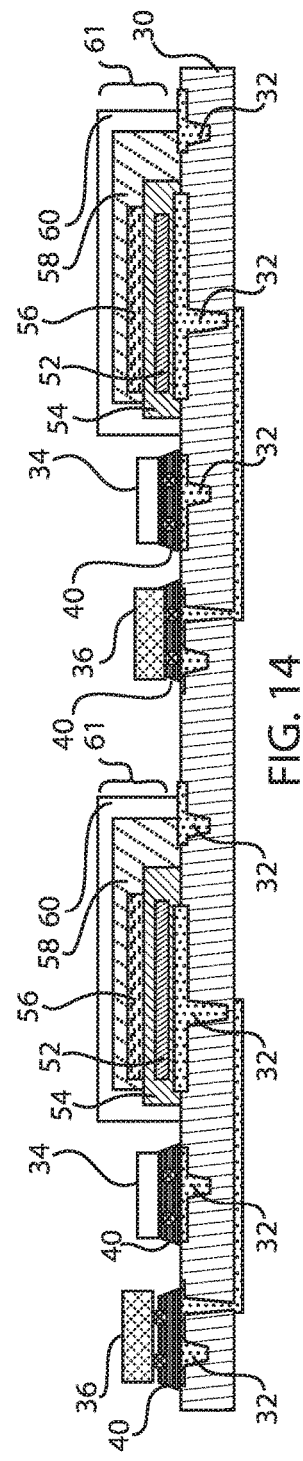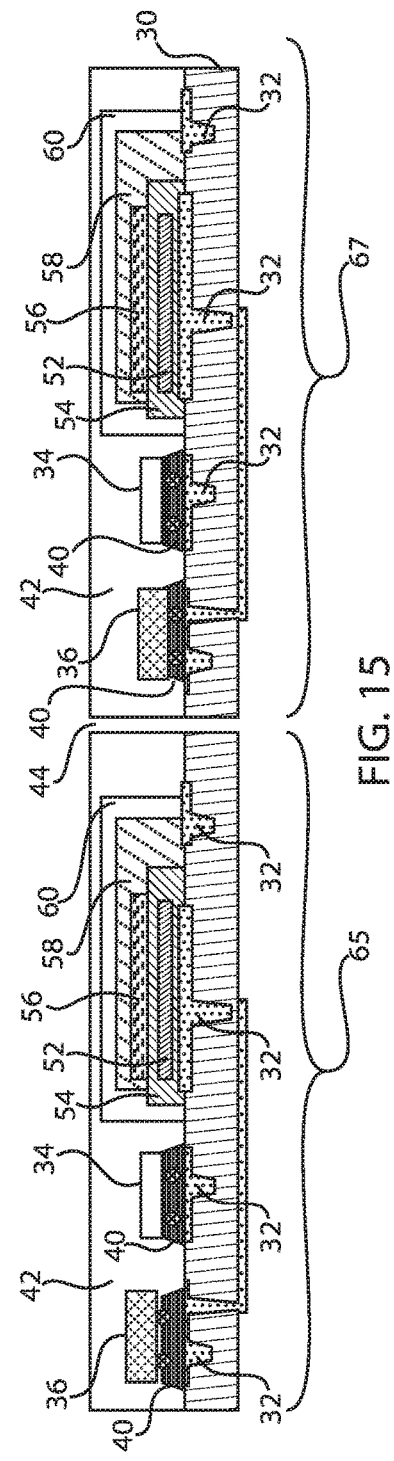

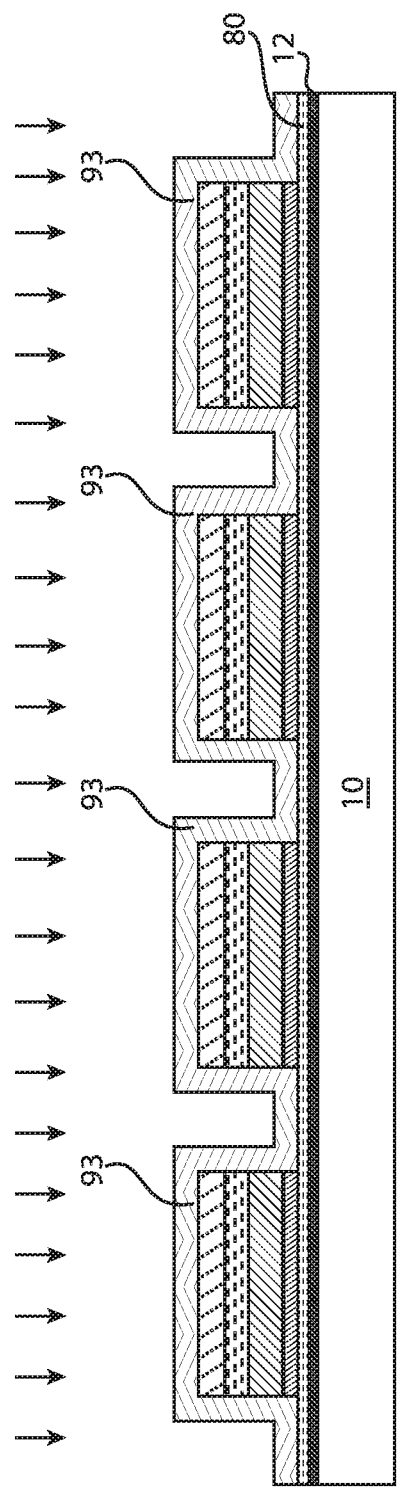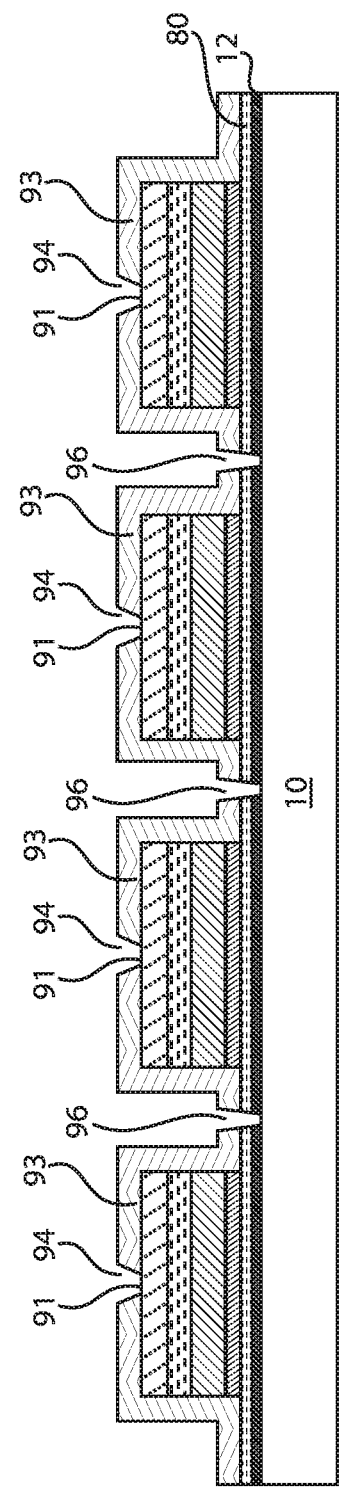

MINIATURIZED ELECTRONICS PACKAGE WITH PATTERNED THIN FILM SOLID STATE BATTERY

BACKGROUND

Technical Field

The present invention relates generally to microsystem architectures, and more specifically, to integrating a thin film microbattery with electronic circuitry.

Description of the Related Art

Solid state lithium-ion microbatteries are generally formed by two electrodes (cathode and anode) separated by an electrolyte. Such a microbattery further includes metal current collectors, made from, e.g., platinum, titanium, copper, or stainless steel. The cathode electrode is made from a compound material having intercalated lithium ions. Examples include $LiCoO_2$ and $Li_2Mn_2O_4$, etc. The electrolyte is a thin film material with a high ionic conductivity. The anode electrode is made for example from metal lithium, tin, or silicon. As materials containing lithium are very sensitive to air, and particularly to oxygen, nitrogen and moisture, they have to be covered with an inert, gas-tight protective barrier. Mastering packaging is a factor that conditions efficiency of microbatteries over time. In addition, handling and assembly of microbatteries is challenging for integration with electronic circuits and devices because of small dimensions and precision requirement.

SUMMARY

In accordance with an embodiment, a structure for integrating a thin film microbattery with electronic circuitry is provided. The structure includes a thin film microbattery formed over a release layer of a handler, wherein subsequent to formation, the thin film microbattery is removed from the handler and deposited onto an interposer, electronic circuitry formed on the interposer, and a seal formed over the thin film microbattery and the electronic circuitry to create individual microbattery modules.

In accordance with an embodiment, a structure for integrating a thin film microbattery with electronic circuitry is provided. The structure includes a thin film microbattery formed directly on an interposer, electronic circuitry formed directly on the interposer after complete formation of the thin-film microbattery, and a seal formed over the thin film microbattery and the electronic circuitry to create individual microbattery modules.

In accordance with an embodiment, a method for integrating a thin film microbattery with electronic circuitry is provided. The method includes forming a release layer over a handler, forming a thin film microbattery over the release layer of the handler, removing the thin film microbattery from the handler, depositing the thin film microbattery on an interposer, forming electronic circuitry on the interposer, and sealing the thin film microbattery and the electronic circuitry to create individual microbattery modules.

It should be noted that the exemplary embodiments are described with reference to different subject-matters. In particular, some embodiments are described with reference to method type claims whereas other embodiments have been described with reference to apparatus type claims. However, a person skilled in the art will gather from the above and the following description that, unless otherwise notified, in addition to any combination of features belonging to one type of subject-matter, also any combination between features relating to different subject-matters, in particular, between features of the method type claims, and features of the apparatus type claims, is considered as to be described within this document.

These and other features and advantages will become apparent from the following detailed description of illustrative embodiments thereof, which is to be read in connection with the accompanying drawings.

BRIEF DESCRIPTION OF THE SEVERAL VIEWS OF THE DRAWINGS

The invention will provide details in the following description of preferred embodiments with reference to the following figures wherein:

FIG. 1 is a cross-sectional view of a release layer formed over a handler, as well as a cathode current collector formed thereon at select locations via a shadow mask, in accordance with the present invention;

FIG. 2 is a cross-sectional view of FIG. 1 where a cathode is formed over the cathode current collector and a solid state electrolyte is formed over the cathode, in accordance with the present invention;

FIG. 3 is a cross-sectional view of FIG. 2 where an anode is formed over the solid state electrolyte and an anode current collector is formed over the anode, in accordance with the present invention;

FIG. 4 is a cross-sectional view of FIG. 3 where a protective coating is applied over the structure, in accordance with the present invention;

FIG. 5 is a cross-sectional view of FIG. 4 where a contact via is formed in the protecting coating to expose a top surface of the anode current collector, in accordance with the present invention;

FIG. 6 is a cross-sectional view of FIG. 5 where the release layer is removed such that the microbattery modules are separated from the handler, in accordance with the present invention;

FIG. 7 is a cross-sectional view of FIG. 6, where electronic circuitry, as well as the microbattery modules are placed on an interposer, in accordance with the present invention;

FIG. 8 is a cross-sectional view of FIG. 7 where an underfill takes place for the electronic circuitry placed on the interposer, in accordance with the present invention;

FIG. 9 is a cross-sectional view of FIG. 8 where a seal is placed over the microbatteries and the electronic circuitry, and a singulation process is implemented, in accordance with the present invention;

FIG. 13 is a cross-sectional view of FIG. 12, where electronic components such as IC die and sensors are placed on the interposer, in accordance with the present invention;

FIG. 14 is a cross-sectional view of FIG. 13, where an underfill takes place for the electronic components on the interposer, in accordance with the present invention;

FIG. 15 is a cross-sectional view of FIG. 14, where a seal is placed over the microbatteries and the electronic components, and a singulation process is implemented, in accordance with the present invention;

FIG. 19 is a cross-sectional view of FIG. 18 where a photolithography process is performed to interconnect the protective layers of the formed microbatteries, in accordance with the present invention;

FIG. 20 is a cross-sectional view of FIG. 19 where vias are formed over and in between the formed microbatteries, in accordance with the present invention;

Throughout the drawings, same or similar reference numerals represent the same or similar elements.

DETAILED DESCRIPTION

Figure 10:
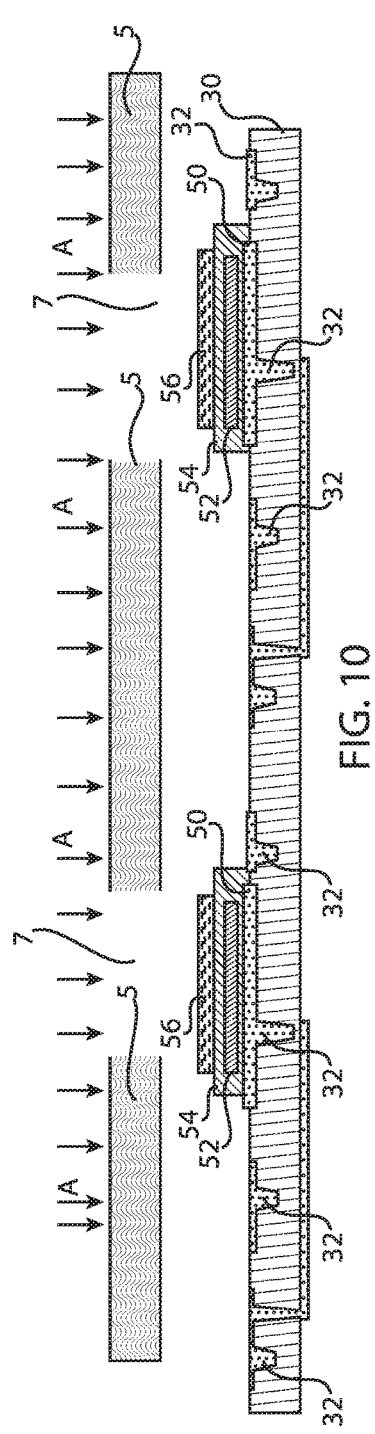
FIG. 10 is a cross-sectional view of a cathode and anode formed over an interposer at select locations via a shadow mask, in accordance with another embodiment of the present invention.

Embodiments in accordance with the present invention provide methods and devices for integrating microbatteries with electronic circuitry to create miniaturized electronic packages. These miniaturized packages can be incorporated into wearable, implantable, or ingestible electronic devices and Internet of Things (IoT) sensors. The microbatteries with electronic circuitry can be manufactured by batch processing techniques. The microbatteries can be manufactured by various sputtering and evaporation techniques. Shadow masks can be applied to pattern the various layers or films of the microbatteries. The manufactured microbatteries can include, e.g., a cathode current collector, a cathode, a solid state electrolyte, an anode, an anode current collector, and a protective coating.

Embodiments in accordance with the present invention provide methods and devices for forming the microbatteries on a handler having a release layer. Subsequent to complete formation of the microbatteries, the release layer is removed to separate the microbatteries from the handler. Once removed, the microbatteries are deposited on an interposer. A plurality of electronic circuitry can then be formed on the interposer and adjacent the microbatteries. The microbatteries and electronic circuitry (microbattery modules) are then sealed and singulation processes are implemented. In various embodiments, the shadow mask can be applied either directly to the handler or be in a non-engaging relationship with respect to the handler.

Embodiments in accordance with the present invention provide methods and devices for incorporating the microbattery modules into a variety of wearable, implantable, or ingestible electronic devices and IoT sensors. The wearable, implantable, or ingestible devices can include at least health and wellness monitoring devices, as well as fitness devices. The wearable, implantable, or ingestible devices can further include at least implantable devices, smart watches, head-mounted devices, security and prevention devices, and gaming and lifestyle devices. The IoT sensors can be incorporated into at least home automation applications, automotive applications, user interface applications, lifestyle and/or entertainment applications, city and/or infrastructure applications, toys, healthcare, fitness, retail tags and/or trackers, platforms and components, etc. The microbattery modules described herein can be incorporated into any type of electronic devices for any type of use or application or operation.

It is to be understood that the present invention will be described in terms of a given illustrative architecture; however, other architectures, structures, substrate materials and process features and steps and/or blocks can be varied within the scope of the present invention. It should be noted that certain features cannot be shown in all figures for the sake of clarity. This is not intended to be interpreted as a limitation of any particular embodiment, or illustration, or scope of the claims.

FIG. 1 is a cross-sectional view of a release layer formed over a handler, as well as a cathode current collector formed thereon at select locations via a shadow mask, in accordance with the present invention.

In various embodiments, a release layer 12 is formed over a handler 10. The handler 10 can be, e.g., a glass handler. A shadow mask 5 is positioned over or adjacent the handler 10 having the release layer 12. A photolithography process is performed to transfer the layers or films of the microbattery in a direction "A." The first deposited layer is a cathode current collector 14. The cathode current collector 14 is formed on select areas of the release layer 12 as defined by the pattern of the shadow mask 5. The pattern includes, e.g., openings 7 through which the cathode current collector 14 is deposited.

FIG. 2 is a cross-sectional view of FIG. 1 where a cathode is formed over the cathode current collector and a solid state electrolyte is formed over the cathode, in accordance with the present invention.

In various embodiments, a cathode 16 is deposited over a portion of the cathode current collector 14. Additionally, a solid state electrolyte 18 is deposited over the cathode 16. In one example, the solid state electrolyte 18 surrounds the cathode 16.

The solid state electrolyte layer 18 can be formed to be in contact with the anode layer 20 (described below) and the cathode layer 16 and can be configured to electrically isolate the anode layer 20 from the cathode layer 16. In one example, the electrolyte layer 18 can be, for example, a lithium phosphorus oxynitride (LiPON).

Suitable materials for the electrolyte layer 18 can further include, but are not limited to, ethylene carbonate and diethyl carbonate containing lithium ion complexes, and other (e.g., acid or alkali) electrolytes having suitable ion transport properties. In lithium ion applications of microbatteries, the electrolyte 18 is usually non-aqueous, in order to avoid reacting with lithium metal components in anode 20 and cathode 16.

Suitable anode 20 and cathode 16 materials include, but are not limited to, lithium, lithium cobalt oxide, lithium iron phosphate and other lithium metal phosphates, lithium manganese oxide, carbon, and graphite, or graphite infused with lithium ions. In one particular configuration, for example, the anode layer 20 can be formed of lithium, and the cathode layer 16 can be formed of lithium cobalt oxide. Alternatively, the anode layer 20 can be formed of lithium cobalt oxide, or another lithium phosphate or metal oxide material, and the cathode layer 16 can be formed of graphite, or lithium ion infused graphite, or a lithium-based material.

FIG. 3 is a cross-sectional view of FIG. 2 where an anode is formed over the solid state electrolyte and an anode current collector is formed over the anode, in accordance with the present invention.

In various embodiments, an anode 20 is formed over a portion of the solid state electrolyte 18. Additionally, an anode current collector 22 is formed over the anode 20. In one example, the anode current collector 22 surrounds the anode 20.

The current collector layers 14, 22 can have a thickness of about 20 to about 1000 nm (e.g., about 20, 50, 100, 150, 200, 250, 300, 350, 400, 450, 500, 550, 600, 650, 700, 750, 800, 850, 900, 950 or 1000 nm), the cathode layer 16 can have a thickness of about 5 to about 5000 nm (e.g., about 5, 10, 20, 50, 100, 200, 300, 400, 500, 1000, 2000, 3000, 4000 or 5000 nm), and the anode layer 20 can have a thickness of about 100 to about 2000 nm (e.g., about 100, 200, 300, 400, 500, 1000 or 2000 nm).

Each of the layers (e.g., current collectors 14, 22, anode 20, cathode 16, electrolyte 18) can be formed using conventional vacuum deposition techniques, which enables direct encapsulation of reactive layers prior to any ambient exposure. Exemplary methods include chemical or physical vapor deposition, flash evaporation, laser ablation and co-evaporation. Physical vapor deposition (PVD) methods can include, for example, reactive or non-reactive sputtering processes. With sputtering, any conventional power supply can be used to generate the ion (e.g., $Ar^+$) current to the target, for example, magnetron, DC, or pulsed DC power supplies. Suitable sputter targets for the various barrier layer compositions can be formed as melted powder or pressed powder targets.

FIG. 4 is a cross-sectional view of FIG. 3 where a protective coating is applied over the structure, in accordance with the present invention.

In various embodiments, a protective coating 24 is applied over the structure. The protective coating 24 contacts the anode current collector 22, the solid state electrolyte 18, and the cathode current collector 14. The protective coating can be, silicon nitride (SiN) or a silicon oxide ($SiO_x$).

FIG. 5 is a cross-sectional view of FIG. 4 where a contact via is formed in the protecting coating to expose a top surface of the anode current collector, in accordance with the present invention.

In various embodiments, a contact via 26 is formed in the protective coating 24 to expose a top surface 23 of the anode current collector 22. The via 26 is formed in order to subsequently provide an electrical connection between the microbattery and other electrical components.

FIG. 6 is a cross-sectional view of FIG. 5 where the release layer is removed such that the microbattery modules are separated from the handler, in accordance with the present invention.

In various embodiments, the release layer 12 is removed such that the microbattery modules 28 are separated from the handler 10. The release layer 12 can be removed by, e.g., a low power laser. Therefore, the microbattery modules 28 are formed via a handler 10 and then removed from the handler 10 to be incorporated onto other electrical interfaces, such as an interposer, described below with reference to FIGS. 7-9.

FIG. 7 is a cross-sectional view of FIG. 6, where electronic circuitry, as well as the microbattery modules are placed on an interposer, in accordance with the present invention.

In various embodiments, the microbattery modules 28 are placed onto an interposer 30. The interposer 30 can include a plurality of connection lines 32 therein. The microbattery modules 28 can be electrically connected to the connection lines 32 of the interposer 30 by, e.g., an epoxy or wire bond or solder paste. The epoxy can be, e.g., a silver epoxy.

Additionally, other electronic circuitry can be placed on the interposer 30. For example, microcontrollers or memories 34 can be placed on the interposer 30. Moreover, sensors 36 can also be placed on the interposer 30 by a component placement mechanism 38. The microcontrollers or memories 34 and the sensors 36 can be electrically connected to the interposer 30 by, e.g., solder bumps 33, 35, respectively. Of course, one skilled in the art can contemplate a plurality of different electrical connection mechanisms for connecting wither the electronic circuitry 34, 36 or the microbattery modules 28 to the interposer 30.

FIG. 8 is a cross-sectional view of FIG. 7 where an underfill takes place for the electronic circuitry placed on the interposer, in accordance with the present invention.

In various embodiments, an underfill 40 takes place. The underfill 40 can be, e.g., an epoxy material. The epoxy material can include, e.g., fine particles of silica. Further, the underfill 40 can be, e.g., an adhesive or dielectric insulator configured to improve reliability of the circuit.

FIG. 9 is a cross-sectional view of FIG. 8 where a seal is placed over the microbatteries and the electronic circuitry, and a singulation process is implemented, in accordance with the present invention.

In various embodiments, a seal 42 is deposited over the microbattery modules 28 and the electronic circuitry 34, 36. The seal 42 can be, e.g., an epoxy material or a polymer.

The seal 42 can be considered a hermetic layer which, for practical purposes, is considered substantially airtight and substantially impervious to moisture. By way of example, the seal 42 can be configured to limit the transpiration (diffusion) of oxygen to less than about $10^{-2}$ $cm^3/m^2/day$ (e.g., less than about $10^{-3}$ $cm^3/m^2/day$), and limit the transpiration (diffusion) of water to about $10^{-2}$ $g/m^2/day$ (e.g., less than about $10^{-3}$, $10^{-4}$, $10^{-5}$ or $10^{-6}$ $g/m^2/day$). In embodiments, the seal 42 substantially inhibits air and water from contacting the layers of the microbattery module 28.

The seal 42 can be formed from one or more of tin oxide, tin phosphate, tin fluorophosphate, tungsten-doped tin fluorophosphate, chalcogenide glass, tellurite glass or borate glass.

The seal 42 according to the present invention can protect lithium (Li) metal and Li ion-based thin film batteries from the external environment, thus substantially minimizing or avoiding adverse reactions with moisture and/or air, and extending battery lifetime. In addition, the seal 42 enables efficient and space-saving packaging and, compared with traditionally-sealed thin film batteries, can be used to produce thin film batteries having enhanced volumetric energy, gravimetric energy and power density.

The seal 42 can have an average thickness of about 2 to about 5 micrometers (e.g., about 2, 3, 4 or 5 micrometers) but, according to embodiments, can range in thickness from about 100 nm to about 35 micrometers (e.g., about 100, 200, 500, 1000, 2000, 5000, 10000, 20000 or 35000 nm).

An etching process 44 can then be performed for implementing singulation. The etching process results in cutting the microbatteries into individual units or modules. After cutting by, e.g. a reactive ion etching (RIE) process, a first microbattery module 45 and a second microbattery module 47 are formed.

FIG. 10 is a cross-sectional view of a cathode and anode formed over an interposer at select locations via a shadow mask, in accordance with another embodiment of the present invention.

In various embodiments, a shadow mask 5 is positioned over or adjacent the interposer 30. A photolithography process is performed to transfer the layers or films of the microbattery in a direction "A." The first deposited layer is a cathode current collector 50. The cathode current collector 50 is formed on select areas of the interposer 30 as defined by the pattern of the shadow mask 5. The pattern includes, e.g., openings 7 through which the cathode current collector 50 is deposited. A cathode 52 is deposited over a portion of the cathode current collector 50. Additionally, a solid state electrolyte 54 is deposited over the cathode 52. In one example, the solid state electrolyte 54 surrounds the cathode 52 and the cathode current collector 50. An anode 56 is then deposited over the solid state electrolyte 54.

Figure 11:
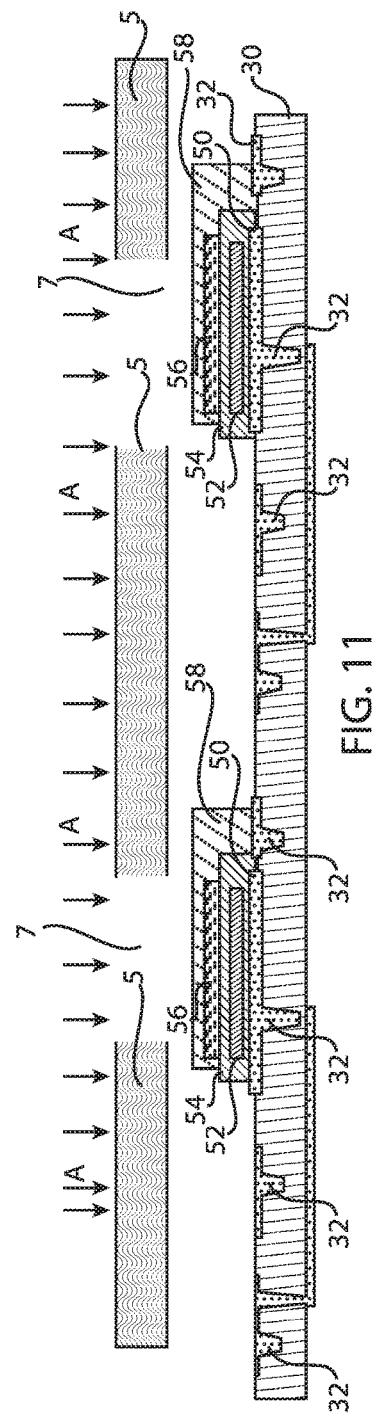
FIG. 11 is a cross-sectional view of FIG. 10, where an anode current collector is formed over the anode, in accordance with the present invention.

FIG. 11 is a cross-sectional view of FIG. 10, where an anode current collector is formed over the anode, in accordance with the present invention.

In various embodiments, an anode current collector 58 is formed over the anode 56. In one example, the anode current collector 58 surrounds the anode 56 and contacts or engages a portion of the solid state electrolyte 54. The anode current collector 58 can extend to contact the electrical connections 32 of the interposer 30.

Figure 12:
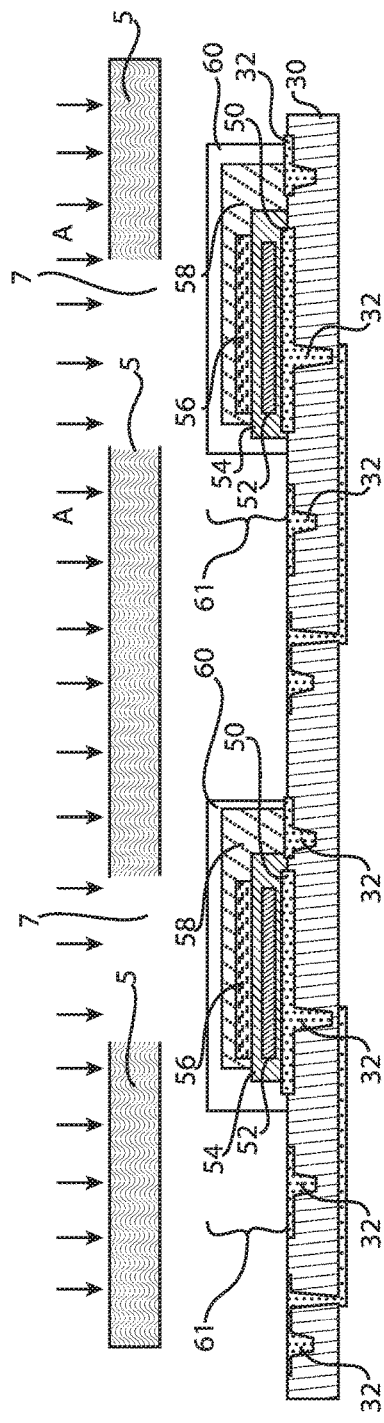
FIG. 12 is a cross-sectional view of FIG. 11, where a protective coating is formed over the structure, in accordance with the present invention.

FIG. 12 is a cross-sectional view of FIG. 11, where a protective coating is formed over the structure, in accordance with the present invention.

In various embodiments, a protective coating 60 is applied over the structure. The protective coating 60 contacts the anode current collector 58 and a portion of the solid state electrolyte 54. Thus, a microbattery 61 is formed over the interposer 30.

FIG. 13 is a cross-sectional view of FIG. 12, where electronic components such as IC die and sensors are placed on the interposer, in accordance with the present invention.

In various embodiments, other electronic circuitry can be placed on the interposer 30. For example, microcontrollers or memories 34 can be placed on the interposer 30. Moreover, sensors 36 can also be placed on the interposer 30 by a component placement mechanism 38. The microcontrollers or memories 34 and the sensors 36 can be electrically connected to the interposer 30 by, e.g., solder bumps 33, 35, respectively. Of course, one skilled in the art can contemplate a plurality of different electrical connection mechanisms for connecting wither the electronic circuitry 34, 36 or the microbattery modules 28 to the interposer 30.

FIG. 14 is a cross-sectional view of FIG. 13, where an underfill takes place for the electronic components on the interposer, in accordance with the present invention.

In various embodiments, an underfill 40 takes place. The underfill 40 can be, e.g., an epoxy material. The epoxy material can include, e.g., fine particles of silica. The underfill 40 can be, e.g., an adhesive or dielectric insulator configured to improve reliability of the circuit.

FIG. 15 is a cross-sectional view of FIG. 14, where a seal is placed over the microbatteries and the electronic components, and a singulation process is implemented, in accordance with the present invention.

In various embodiments, a seal 42 is deposited over the microbattery modules 61 and the electronic circuitry 34, 36. The seal 42 can be, e.g., an epoxy material or a polymer. An etching process 44 can then be performed for implementing singulation. The etching process results in cutting the microbatteries into individual units or modules. After cutting by, e.g. a reactive ion etching (RIE) process, a first microbattery module 65 and a second microbattery module 67 are formed.

Figure 16:
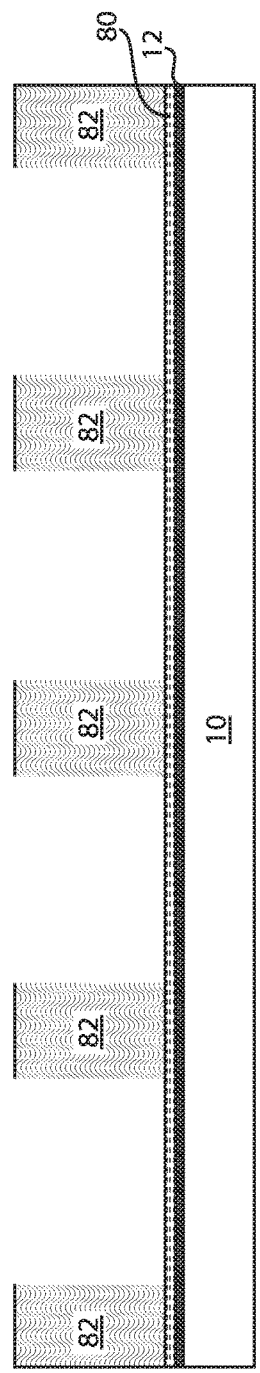
FIG. 16 is a cross-sectional view of a photoresist formed over a handler, in accordance with another embodiment of the present invention.

FIG. 16 is a cross-sectional view of a photoresist formed over a handler, in accordance with another embodiment of the present invention.

In various embodiments, a release layer 12 is formed over a handler 10. A cathode current collector 80 is formed over the release layer 12. Additionally, a photoresist 82 is placed over select portions of the cathode current collector 80.

Figure 17:
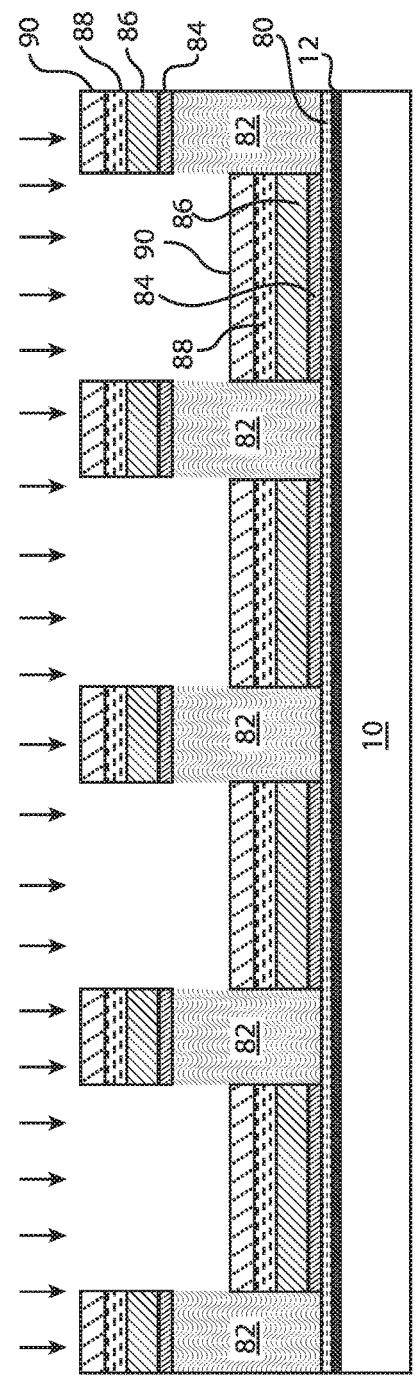
FIG. 17 is a cross-sectional view of FIG. 16 where a cathode, an anode, and an electrolyte are deposited over the photoresist, in accordance with the present invention.

FIG. 17 is a cross-sectional view of FIG. 16 where a cathode, an anode, and an electrolyte are deposited over the photoresist, in accordance with the present invention.

In various embodiments, a cathode 84, a solid state electrolyte 86, an anode 88, and an anode current collector 90 are deposited over the photoresist 82, as well as over exposed sections of the cathode current collector 80.

Figure 18:
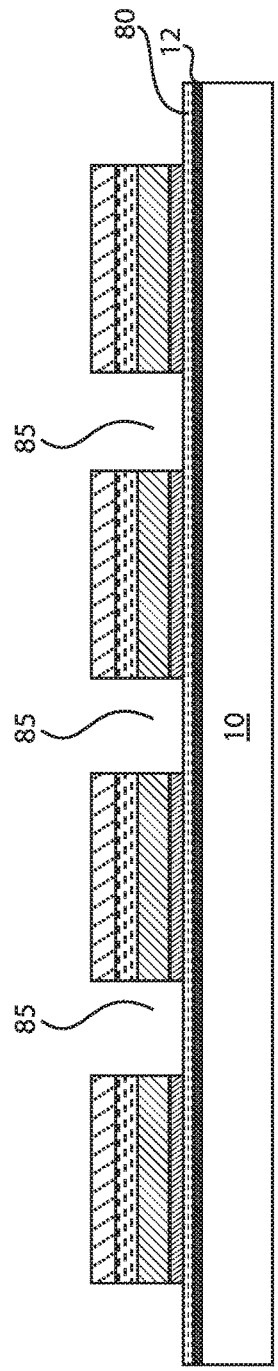
FIG. 18 is a cross-sectional view of FIG. 17 where the photoresist are removed, in accordance with the present invention.

FIG. 18 is a cross-sectional view of FIG. 17 where the photoresist are removed, in accordance with the present invention.

In various embodiments, the photoresist is etched to expose a top surface of the cathode current collector 80. Thus, gaps 85 are formed between the microbattery structures.

FIG. 19 is a cross-sectional view of FIG. 18 where a photolithography process is performed to interconnect the protective layers of the formed microbatteries, in accordance with the present invention.

In various embodiments, a photolithography process takes place to connect the protective layers to form protective layer 93 extending over all the microbattery structures.

FIG. 20 is a cross-sectional view of FIG. 19 where vias are formed over and in between the formed microbatteries, in accordance with the present invention.

In various embodiments, vias 94 are formed over each of the microbattery structures to expose a top surface 91 of the anode current collector 90. Additionally, vias 96 are formed between the microbattery structures to separate the microbattery structures into individual microbattery modules 99. The microbattery modules 99 can now be separated from the handler 10 by removing the release layer 12, and placed over, e.g., an interposer to be integrated with other electronic circuitry.

Figure 21:
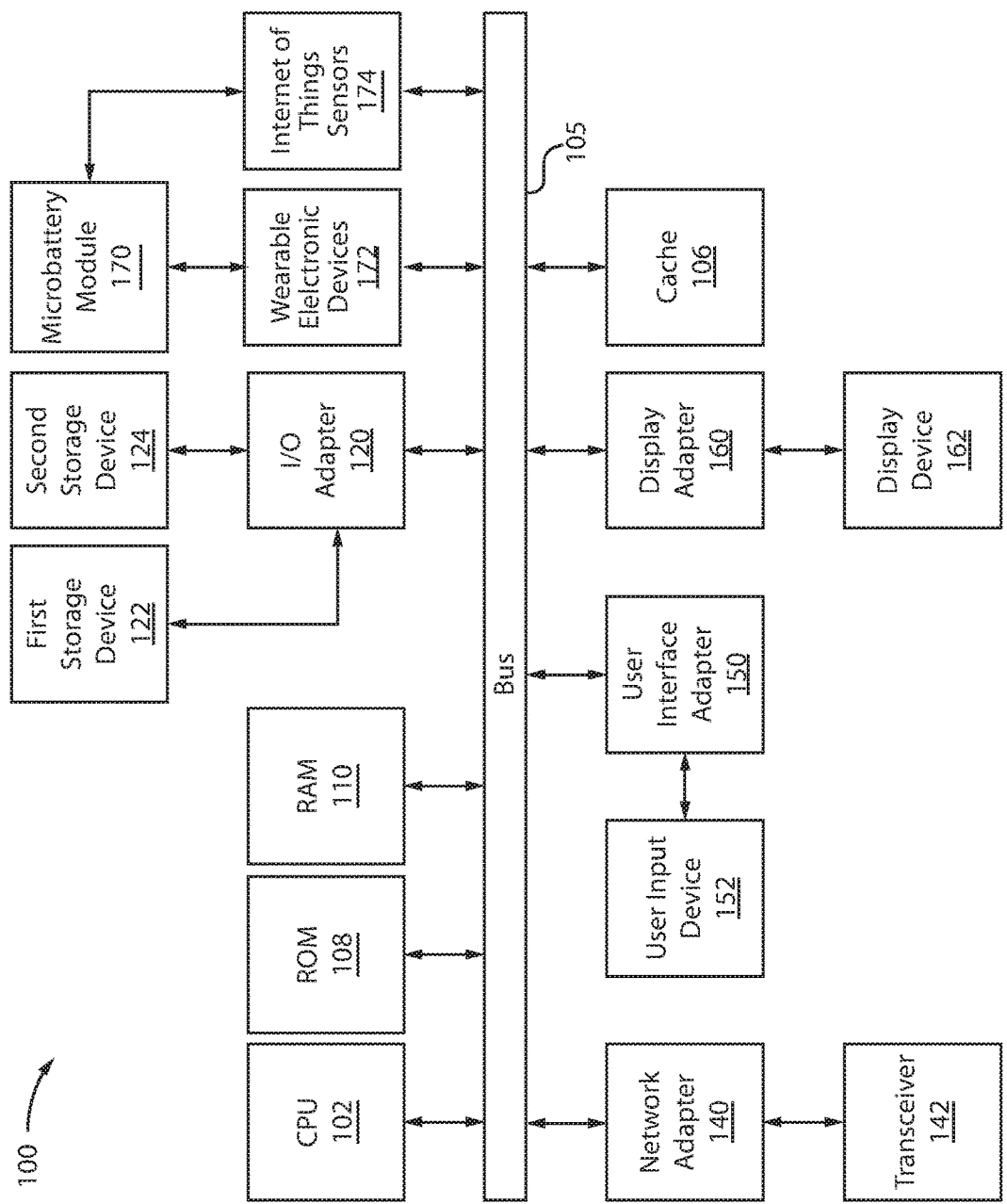
FIG. 21 is an exemplary computer processing system to which the present microbattery modules can be applied to, in accordance with the present invention.

FIG. 21 is an exemplary computer processing system to which the present microbattery modules can be applied to, in accordance with the present invention.

An exemplary computer processing system 100 to which the present invention may be applied is shown in accordance with one embodiment. The processing system 100 includes at least one processor (CPU) 102 operatively coupled to other components via a system bus 105. A cache 106, a Read Only Memory (ROM) 108, a Random Access Memory (RAM) 110, an input/output (I/O) adapter 120, a microbattery module 170, a network adapter 140, a user interface adapter 150, and a display adapter 160, are operatively coupled to the system bus 105.

A first storage device 122 and a second storage device 124 are operatively coupled to system bus 105 by the I/O adapter 120. The storage devices 122 and 124 can be any of a disk storage device (e.g., a magnetic or optical disk storage device), a solid state magnetic device, and so forth. The storage devices 122 and 124 can be the same type of storage device or different types of storage devices.

The microbattery module 170 can be incorporated into wearable electronic devices 172 and incorporated into Internet of Things (IoT) sensors 174.

A transceiver 142 is operatively coupled to system bus 105 by network adapter 140. A display device 162 is operatively coupled to system bus 105 by display adapter 160.

A user input device 152 is operatively coupled to system bus 105 by user interface adapter 150. The user input device 152 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present invention. The user input device 152 can be the same type of user input device or different types of user input devices. The user input device 152 can be used to input and output information to and from computer processing system 100.

Of course, the computer processing system 100 can also include other elements (not shown), as readily contemplated by one of skill in the art, as well as omit certain elements. For example, various other input devices and/or output devices can be included in computer processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the computer processing system 100 are readily contemplated by one of ordinary skill in the art given the teachings of the present invention provided herein.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Figure 22:
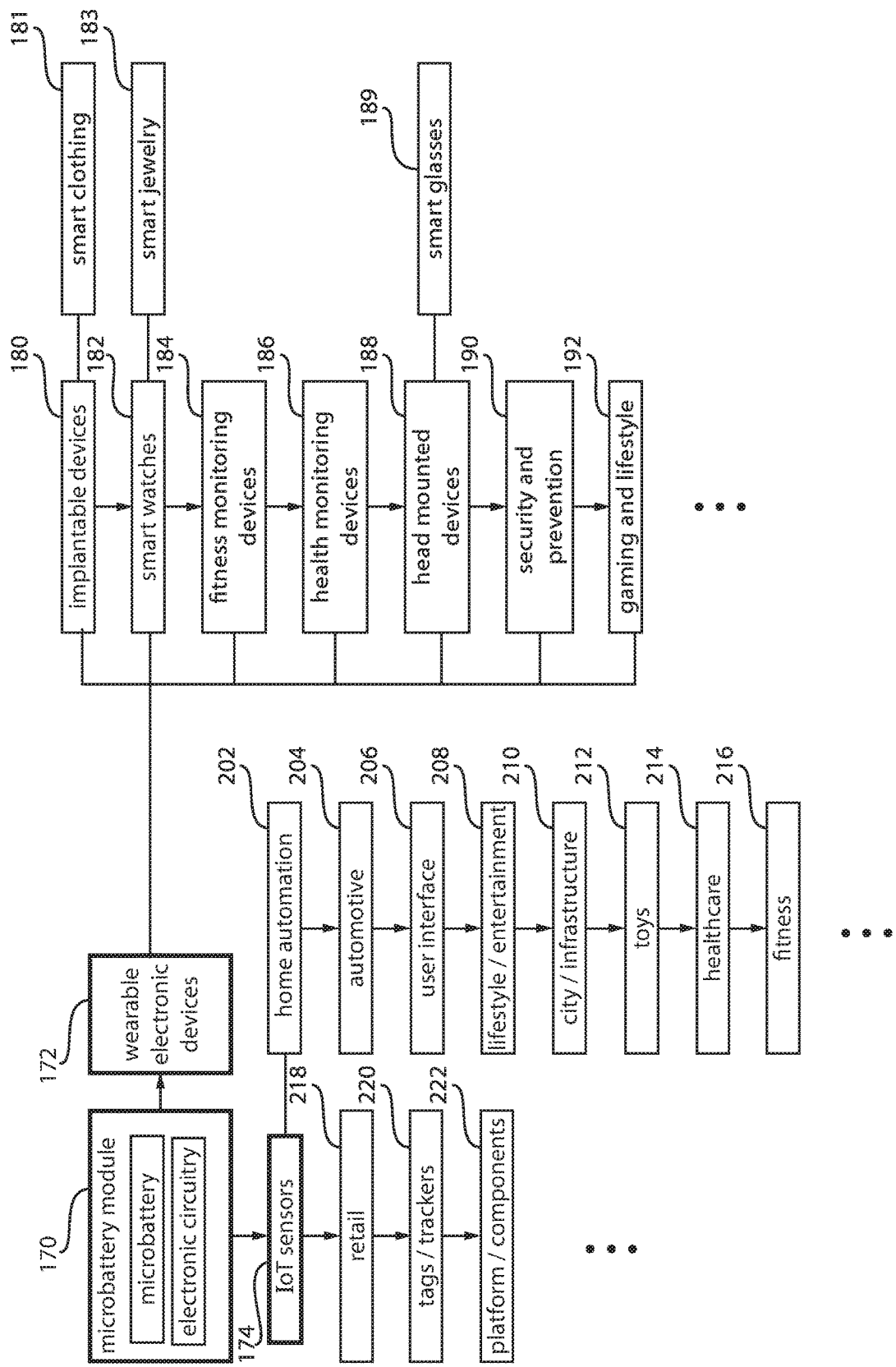
FIG. 22 is a block/flow diagram illustrating the microbattery modules described herein incorporated into wearable, implantable, or ingestible electronic devices and compatible with Internet of Things (IoT) sensors and applications, in accordance with the present invention.

FIG. 22 is a block/flow diagram illustrating the microbattery modules described herein incorporated into wearable electronic devices and compatible with Internet of Things (IoT) sensors and applications, in accordance with the present invention.

In various embodiments, the microbattery module 170 of the present invention can be incorporated into a variety of different devices and/or systems. For example, the microbattery module 170 can be incorporated into wearable electronic devices 172. Wearable electronic devices 172 can include implantable devices 180, such as smart clothing 181. Wearable devices 172 can include smart watches 182, as well as smart jewelry 183. Wearable devices 172 can further include fitness monitoring devices 184, health and wellness monitoring devise 186, head-mounted devices 188 (e.g., smart glasses 189), security and prevention systems 190, and gaming and lifestyle devices 192.

The microbattery module 170 of the present invention can be further incorporated into Internet of Thing (IoT) sensors 174 for various applications, such as home automation 202, automotive 204, user interface 206, lifestyle and/or entertainment 208, city and/or infrastructure 210, toys 212, healthcare 214, fitness 216, retail 218, tags and/or trackers 220, and/or platform and components 222. Of course, one skilled in the art can contemplate incorporating such microbattery modules formed therein into any type of electronic devices for any types of applications, not limited to the ones described herein.

It is to be understood that the present invention will be described in terms of a given illustrative architecture; however, other architectures, structures, substrate materials and process features and steps and/or blocks can be varied within the scope of the present invention.

It will also be understood that when an element such as a layer, region or substrate is referred to as being "on" or "over" another element, it can be directly on the other element or intervening elements can also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements can be present. In contrast, when an element is referred to as being "directly connected" or "directly coupled" to another element, there are no intervening elements present.

The present embodiments can include a design for an integrated circuit chip, which can be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer can transmit the resulting design by physical mechanisms (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which include multiple copies of the chip design in question that are to be formed on a wafer. The photolithographic masks are utilized to define areas of the wafer (and/or the layers thereon) to be etched or otherwise processed.

Methods as described herein can be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

It should also be understood that material compounds will be described in terms of listed elements, e.g., SiGe. These compounds include different proportions of the elements within the compound, e.g., SiGe includes $Si_xGe_{1-x}$ where x is less than or equal to 1, etc. In addition, other elements can be included in the compound and still function in accordance with the present embodiments. The compounds with additional elements will be referred to herein as alloys.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This can be extended, as readily apparent by one of ordinary skill in this and related arts, for as many items listed.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, such as "beneath," "below," "lower," "above," "upper," and the like, can be used herein for ease of description to describe one element's or feature's relationship to another element(s) or feature(s) as illustrated in the FIGS. It will be understood that the spatially relative terms are intended to encompass different orientations of the device in use or operation in addition to the orientation depicted in the FIGS. For example, if the device in the FIGS. is turned over, elements described as "below" or "beneath" other elements or features would then be oriented "above" the other elements or features. Thus, the term "below" can encompass both an orientation of above and below. The device can be otherwise oriented (rotated 90 degrees or at other orientations), and the spatially relative descriptors used herein can be interpreted accordingly. In addition, it will also be understood that when a layer is referred to as being "between" two layers, it can be the only layer between the two layers, or one or more intervening layers can also be present.

It will be understood that, although the terms first, second, etc. can be used herein to describe various elements, these elements should not be limited by these terms. These terms are only used to distinguish one element from another element. Thus, a first element discussed below could be termed a second element without departing from the scope of the present concept.

Having described preferred embodiments of a structure and composition of a flexible thin film microbattery and integration of such microbattery with electronic circuitry to form microbattery modules (which are intended to be illustrative and not limiting), it is noted that modifications and variations can be made by persons skilled in the art in light of the above teachings. It is therefore to be understood that changes may be made in the particular embodiments described which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for integrating a thin film microbattery with electronic circuitry, the method comprising:
    forming a release layer over a handler;
    forming a thin film microbattery over the release layer of the handler;
    removing the thin film microbattery from the handler;
    depositing the thin film microbattery on an interposer;
    disposing electronic circuitry on the interposer, all the electronic circuitry being collinear with respect to each other and with the thin film microbattery;
    wherein the thin film microbattery is disposed directly between the electronic circuitry; and
    sealing the thin film microbattery and the electronic circuitry to create individual microbattery modules.

2. The method of claim 1, further comprising electrically connecting the thin film microbattery and the electronic circuitry by electrical connections formed within the interposer.

3. The method of claim 1, further comprising removing the thin film microbattery from the handler by a low-power laser device.

4. The method of claim 1, further comprising forming the thin film microbattery via a shadow mask positioned either in a non-engaging relationship with the handler or in direct contact with the handler.

5. The method of claim 1, further comprising incorporating the microbattery modules into wearable, implantable, ingestible electronic devices.

6. The method of claim 5, wherein the wearable, implantable, ingestible electronic devices enable at least health and fitness monitoring.

\* \* \* \* \*